US012640237B2

(12) United States Patent
    Greenfield

(10) Patent No.: US 12,640,237 B2
(45) **Date of Patent: *May 26, 2026**

(54) DATA PROCESSING SYSTEM AND METHOD

(71) Applicant: Petagene Ltd., Cambridge (GB)

(72) Inventor: Daniel Leo Greenfield, Cambridge (GB)

(73) Assignee: Petagene Ltd., Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/886,651

(22) Filed: Aug. 12, 2022

(65) Prior Publication Data

US 2022/0383988 A1     Dec. 1, 2022

Related U.S. Application Data

(63) Continuation of application No. 16/616,307, filed as application No. PCT/EP2018/063741 on May 24, 2018, now Pat. No. 11,443,833.

(30) Foreign Application Priority Data

May 24, 2017 (GB) ...................................... 1708340

(51) Int. Cl.
    *G16B 50/50*      (2019.01)
    *G06F 9/445*      (2018.01)
    *G06F 16/188*     (2019.01)

(52) U.S. Cl.
    CPC ......... *G16B 50/50* (2019.02); *G06F 9/44521* (2013.01); *G06F 16/188* (2019.01)

(58) Field of Classification Search
    CPC .... G06F 9/44521; G06F 16/188; G16B 50/50
    See application file for complete search history.

(56) References Cited

U.S. PATENT DOCUMENTS 7,356,679 B1    4/2008  Le et al.
8,209,680 B1 *  6/2012  Le ......................... G06F 16/188
                                                        713/1

(Continued)

FOREIGN PATENT DOCUMENTS

CN    201880034435.4      1/2023
GB    2 404 262 A         4/2018

(Continued)

OTHER PUBLICATIONS

Dynamic Linker, Wikipedia (May 4, 2017) retrieved from https://en.wikipedia.org/w/index.php?title=Dynamic_linker&oldid=778702419 (Year: 2017).*

(Continued)

*Primary Examiner* — Lewis A Bullock, Jr.
*Assistant Examiner* — Theodore E Hebert
(74) *Attorney, Agent, or Firm* — Wolf, Greenfield & Sacks, P.C.

(57)     ABSTRACT

A data processing system includes a data processing arrangement, wherein the data processing arrangement includes computing hardware for executing one or more software products, wherein execution of the one or more software products configures the data processing arrangement to access data from a file system arrangement. The data processing arrangement is operable to load a dynamic linker that is operable to include an intercept library that intercepts file access operations of an executable software product wherein: (i) a virtual file that does not exist on the file system arrangement becomes accessible to the executable software product; (ii) the virtual file is a result of either (a) a just-in-time translation of one or more real files of the file system arrangement, wherein the just-in-time translation is made from one file format to another file format, or (b) conversion of the access operation to an equivalent cloud (Continued)

Providing a data processing system including a data processing arrangement, wherein the data processing arrangement includes computing hardware for executing one or more software products, wherein execution of the one or more software products configures the data processing arrangement to access data from a file system arrangement,
200

Operating the data processing arrangement to load a dynamic linker that is operable to include an intercept library that intercepts file access operations of an executable software product wherein:

(i) a virtual file that does not exist on the file system arrangement becomes accessible to the executable software product;

(ii) the virtual file is a result of either (a) a just-in-time translation of one or more real files of the file system arrangement, wherein the just-in-time translation is made from one file format to another file format, or (b) conversion of the access operation to an equivalent cloud object-storage access operation(s) on a real object located on the cloud object-storage, or (c) a combination of the just-in-time translation of (a) with the object access conversion from (b); and (iii) optionally, wherein the virtual file is a different file format to the real file/object, wherein a compressed file format and the virtual file are mutually different file format; and (iv) optionally, the file formats are genomic file formats

210 object-storage access operation(s) on a real object located on the cloud object-storage, or (c) a combination of the just-in-time translation of (a) with the object access conversion from (b). Optionally, at least one of: (iii) the virtual file is a different file format to the real file/object, wherein a compressed file format and the virtual file are mutually different file formats; and (iv) the file formats are genomic file formats.

18 Claims, 2 Drawing Sheets

(56) References Cited

U.S. PATENT DOCUMENTS

| | | | |
|---|---|---|---|
| 8,612,971 B1 | 12/2013 | Fitzgerald et al. | |
| 10,230,390 B2 * | 3/2019 | Leighton | G16B 30/00 |
| 10,630,812 B2 * | 4/2020 | Anderson | H04L 9/0861 |
| 11,176,103 B2 * | 11/2021 | Greenfield | G06F 16/2228 |
| 11,244,742 B2 * | 2/2022 | Greenfield | G16B 50/00 |
| 11,443,833 B2 * | 9/2022 | Greenfield | G16B 50/00 |
| 2002/0019887 A1 * | 2/2002 | Moore | G06F 9/46 |
| | | | 719/328 |
| 2008/0134175 A1 | 6/2008 | Fitzgerald et al. | |
| 2008/0250400 A1 * | 10/2008 | Vertes | G06F 9/4486 |
| | | | 712/E9.083 |
| 2011/0004586 A1 * | 1/2011 | Cherryholmes | G06F 11/1471 |
| | | | 707/682 |
| 2011/0289513 A1 * | 11/2011 | Degirmenci | G06F 9/542 |
| | | | 719/313 |
| 2012/0005237 A1 * | 1/2012 | Obata | G06F 16/188 |
| | | | 707/798 |
| 2012/0226742 A1 * | 9/2012 | Momchilov | G06F 3/048 |
| | | | 709/203 |
| 2012/0324365 A1 * | 12/2012 | Momchilov | H04L 67/01 |
| | | | 715/738 |
| 2014/0137184 A1 * | 5/2014 | Russello | G06F 21/60 |
| | | | 726/1 |
| 2014/0229921 A1 * | 8/2014 | Arora | G06F 11/3644 |
| | | | 717/125 |
| 2016/0196149 A1 * | 7/2016 | Liddicott | G06F 9/4482 |
| | | | 718/102 |
| 2016/0344849 A1 * | 11/2016 | Thomas | G16B 30/20 |
| 2016/0352699 A1 * | 12/2016 | Sinclair | G16C 99/00 |
| 2017/0177597 A1 * | 6/2017 | Asimenos | G06F 16/188 |
| 2018/0089224 A1 * | 3/2018 | Muthuswamy | G06F 16/13 |
| 2018/0101547 A1 * | 4/2018 | Greenfield | G06F 16/2228 |
| 2018/0152535 A1 * | 5/2018 | Sade | G16B 50/50 |
| 2018/0225447 A1 * | 8/2018 | Pintiysky | G06F 21/566 |
| 2018/0357068 A1 * | 12/2018 | Ambichl | G06F 9/545 |
| 2020/0117483 A1 * | 4/2020 | Greenfield | G06F 9/44521 |

FOREIGN PATENT DOCUMENTS

| | | | | |
|---|---|---|---|---|
| GB | 2554883 A | 4/2018 | | |
| WO | WO 00/014632 A1 | 3/2000 | | |
| WO | WO 02/44850 A2 | 6/2002 | | |
| WO | WO-2016185459 A1 * | 11/2016 | | G16B 30/00 |

OTHER PUBLICATIONS

Spillane et al., ACM (Jun. 2007) retrieved from https://www.usenix. org/legacy/events/expcs07/papers/22-spillane.pdf (Year: 2007).*

Chinese Office Action for Chinese Application No. 201880034435.4 dated Jan. 19, 2023.

International Preliminary Report on Patentability for International Application No. PCT/EP2018/063741 mailed Dec. 5, 2019.

International Search Report and Written Opinion for International Application No. PCT/EP2018/063741 mailed Sep. 12, 2018.

[No Author Listed], Dynamic Linker. Wikipedia. May 4, 2017. https://en.wikipedia.org/w/index.php?title=Dynamic_linker&oldid= 778702419 [last accessed May 20, 2021]. 4 pages.

[No Author Listed], Dynamic recompilation. Wikipedia. Sep. 28, 2016. https://en.wikipedia.org/w/index.php?title=Dynamic_ recompilation&oldid=741515514 [last accessed May 20, 2021]. 5 pages.

[No Author Listed], How to intercept file system access inside dlopen()?. Stackoverflow. Oct. 17, 2011. https://stackoverflow.com/ questions/7699583/how-to-intercept-file-system-access-inside-dlopen [last accessed May 20, 2021]. 3 pages.

[No Author Listed], Memory-mapped file. Wikipedia. Apr. 2, 2017. https://en.wikipedia.org/w/index.php?title=Memorymapped_file &oldid=%20773474038 [last accessed May 20, 2021]. 5 pages.

[No Author Listed], Page replacement algorithm. Wikipedia. Apr. 2, 20175. https://en.wikipedia.org/w/index.php?title=Page_replacement_ algorithm&oldid=777177156 [last accessed May 20, 2021]. 11 pages.

[No Author Listed], ptrace. Wikipedia. Mar. 20, 2017. https://en. wikipedia.org/w/index.php?title=Ptrace&oldid=771247271 [last accessed May 20, 2021]. 4 pages.

[No Author Listed], uncompress.so. Delorie.com. Jan. 7, 2017. https://web.archive.org/web/20170107193216/http://www.delorie. com/gnu/docs/zlibc/zlibc.3.ht ml [last accessed May 20, 2021]. 8 pages.

Wang et al., WaFS: a workflow-aware file system for effective storage utilization in the cloud. IEEE Transactions on Computers. Sep. 2015;64(9):2716-29.

* cited by examiner

Figure 2:
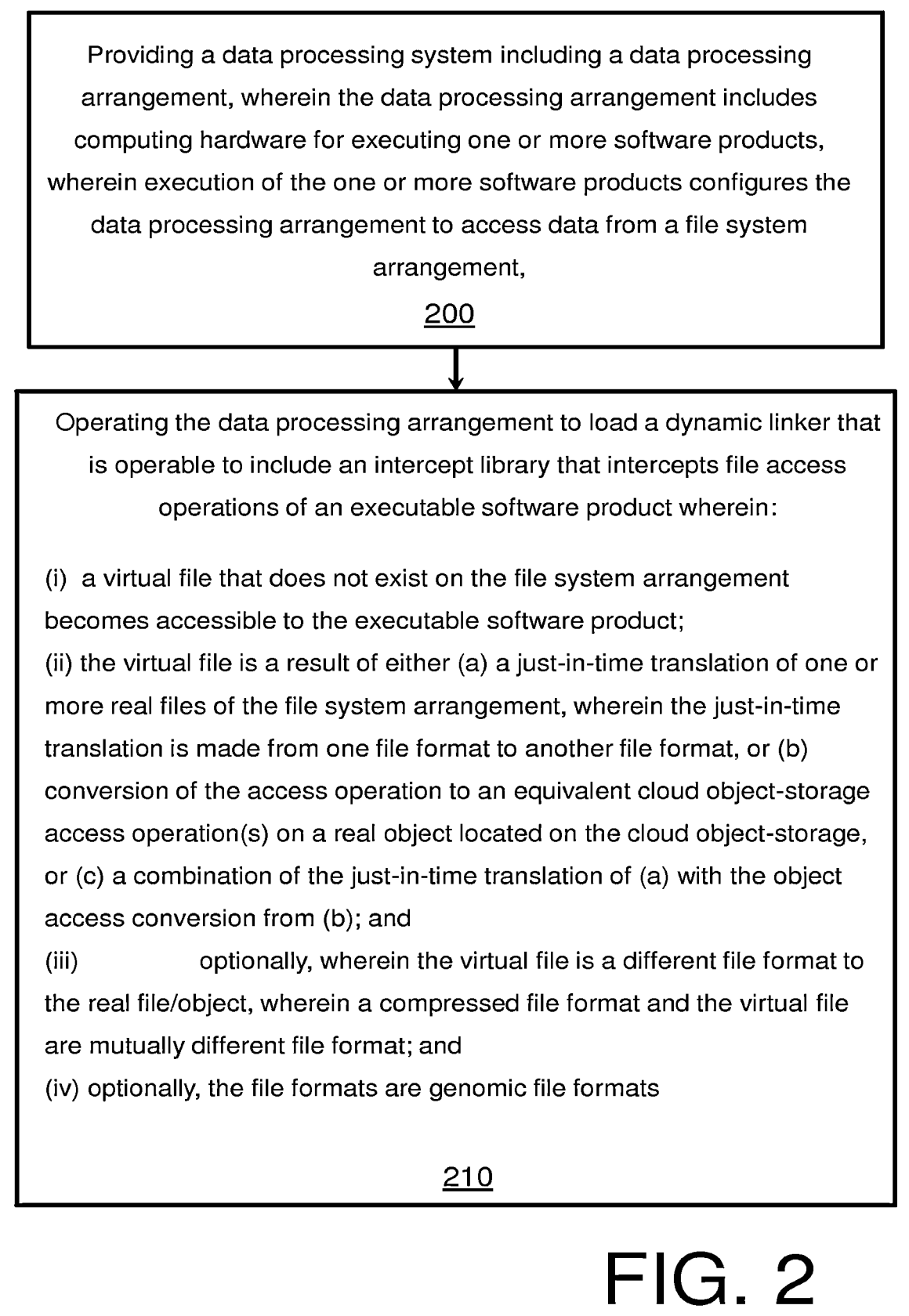

Providing a data processing system including a data processing arrangement, wherein the data processing arrangement includes computing hardware for executing one or more software products, wherein execution of the one or more software products configures the data processing arrangement to access data from a file system arrangement,

200

Operating the data processing arrangement to load a dynamic linker that is operable to include an intercept library that intercepts file access operations of an executable software product wherein:

(i)  a virtual file that does not exist on the file system arrangement becomes accessible to the executable software product;

(ii) the virtual file is a result of either (a) a just-in-time translation of one or more real files of the file system arrangement, wherein the just-in-time translation is made from one file format to another file format, or (b) conversion of the access operation to an equivalent cloud object-storage access operation(s) on a real object located on the cloud object-storage, or (c) a combination of the just-in-time translation of (a) with the object access conversion from (b); and (iii)              optionally, wherein the virtual file is a different file format to the real file/object, wherein a compressed file format and the virtual file are mutually different file format; and (iv) optionally, the file formats are genomic file formats

DATA PROCESSING SYSTEM AND METHOD

RELATED APPLICATIONS

This application claims priority under 35 U.S.C. § 120 and is a continuation of U.S. patent application Ser. No. 16/616,307, filed on Nov. 22, 2019, and titled, "DATA PROCESSING SYSTEM AND METHOD" which is a National Stage entry under 35 U.S.C. § 371 of International Patent Application No., PCT/EP2018/063741 filed on May 24, 2018, and titled, "DATA PROCESSING SYSTEM AND METHOD" which claims benefit of priority to United Kingdom Patent Application Serial No. 1708340.3, filed on May 24, 2017, and titled "DATA PROCESSING SYSTEM AND METHOD."

TECHNICAL FIELD

The present disclosure relates to data processing systems. Moreover, the present disclosure concerns methods of using aforesaid data processing systems for processing data, for example for processing genomics data. Yet additionally, the present disclosure is concerned with computer program products comprising non-transitory computer-readable storage media having computer-readable instructions stored thereon, the computer-readable instructions being executable by a computerized device comprising processing hardware to execute the aforesaid methods.

BACKGROUND

Contemporary data processing systems are often required to access data stored in one or more repositories when performing data processing functions; the repositories of data can include, for example, genomic data. The data processing systems are operable to function under software control, by executing one or more software products.

In generating software products, it is contemporary practice to employ a linker to compile various items of software to generate executable software code. The executable software code is known as a software product. Moreover, various types of linkers are known, for example as described in Wikipedia, wherein a dynamic linker can be influenced into modifying its behaviour during either a given program's execution or linking of the given program, and examples of a dynamic linker can be found described in run-time linker manual pages for various Unix-like systems; UNIX® is a trademark. A typical modification of a behaviour of such a dynamic linker is provided in:

LD_LIBRARY_PATH and LD_PRELOAD environment variables, wherein the dynamic linker adjusts a runtime linking process by searching for shared libraries at alternate locations and by forcibly loading and linking libraries that would otherwise not be loaded and linked, respectively. An example of modifying an executable behaviour via a dynamic linker is zlibc, also known as "uncompress.so", which facilitates transparent decompression when used through the LD_PRELOAD hack; as a result, it is possible to read a pre-compressed (gzipped) file data on BSD and Linux® systems as if the files were not compressed, essentially allowing a given user to add transparent decompression to an underlying file system, although with some caveats. In order to achieve such a functionality, a mechanism is employed that is flexible, allowing trivial adaptation of a same given code to perform additional or alternate processing of data during a given file read, prior to a provision of data to a given user process that has requested it.

However, contemporary known dynamic linkers do not perform adequately well in data processing systems to allow a wide variety of data in repositories to be modified in a dynamic manner.

SUMMARY

The present disclosure seeks to provide an improved data processing system that is able to translate file accesses, for example to compressed genomic data or to cloud object storage, in a more flexible and dynamic manner.

In a first aspect, there is provided a data processing system including a data processing arrangement, wherein the data processing arrangement includes computing hardware for executing one or more software products, wherein execution of the one or more software products configures the data processing arrangement to access data from a file system arrangement, characterized in that the data processing arrangement is operable to load a dynamic linker that is operable to include an intercept library that intercepts file access operations of an executable software product wherein:

(i) a virtual file that does not exist on the file system arrangement becomes accessible to the executable software product;

(ii) the virtual file is a result of either (a) a just-in-time translation of one or more real files of the file system arrangement, wherein the just-in-time translation is made from one file format to another file format, or (b) conversion of the access operation to an equivalent cloud object-storage access operation(s) on a real object located on the cloud object-storage, or (c) a combination of the just-in-time translation of (a) with the object access conversion from (b).

Optionally, in the data processing system, at least one of:

(iii) the virtual file is a different file format to the real file/object, wherein a compressed file format and the virtual file are mutually different file formats; and (iv) the file formats are genomic file formats.

The invention is of advantage in that the dynamic linker, via use of the intercept library, is operable to cause the data processing system to be more versatile in utilizing dynamically changing data files and data file formats when performing computations, for example computations upon acquired data from sensor arrangements, for example associated with genomic readout.

In a second aspect, there is provided a method of using a data processing system including a data processing arrangement, wherein the data processing arrangement includes computing hardware for executing one or more software products, wherein execution of the one or more software products configures the data processing arrangement to access data from a file system arrangement, characterized in that the method includes operating the data processing arrangement to load a dynamic linker that is operable to include an intercept library that intercepts file access operations of an executable software product wherein:

(i) a virtual file that does not exist on the file system arrangement becomes accessible to the executable software product;

(ii) the virtual file is a result of either (a) a just-in-time translation of one or more real files of the file system arrangement, wherein the just-in-time translation is made from one file format to another file format, or (b) conversion of the access operation to an equivalent cloud object-storage access operation(s) on a real object located on the cloud object-storage, or (c) a combination of the just-in-time translation of (a) with the object access conversion from (b).

Optionally, in the method, at least one of:

(iii) the virtual file is a different file format to the real file/object, wherein a compressed file format and the virtual file are mutually different file formats; and (iv) the file formats are genomic file formats.

Optionally, in the data processing system, at least one of:

(iii) the virtual file is a different file format to the real file/object, wherein a compressed file format and the virtual file are mutually different file formats; and (iv) the file formats are genomic file formats.

In a third aspect, embodiments of the present disclosure provide a computer program product comprising a non-transitory computer-readable storage medium having computer-readable instructions stored thereon, the computer-readable instructions being executable by a computerized device comprising processing hardware to execute a method pursuant to the aforementioned second aspect.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and apparatus disclosed herein. Moreover, those in the art will understand that the drawings are not to scale. Wherever possible, like elements have been indicated by identical numbers.

Embodiments of the present disclosure will now be described, by way of example only, with reference to the following diagram wherein:

FIG. 2 is an illustration of a flow diagram of a method of (for) operating the data processing system of FIG. 1.

Figure 1:
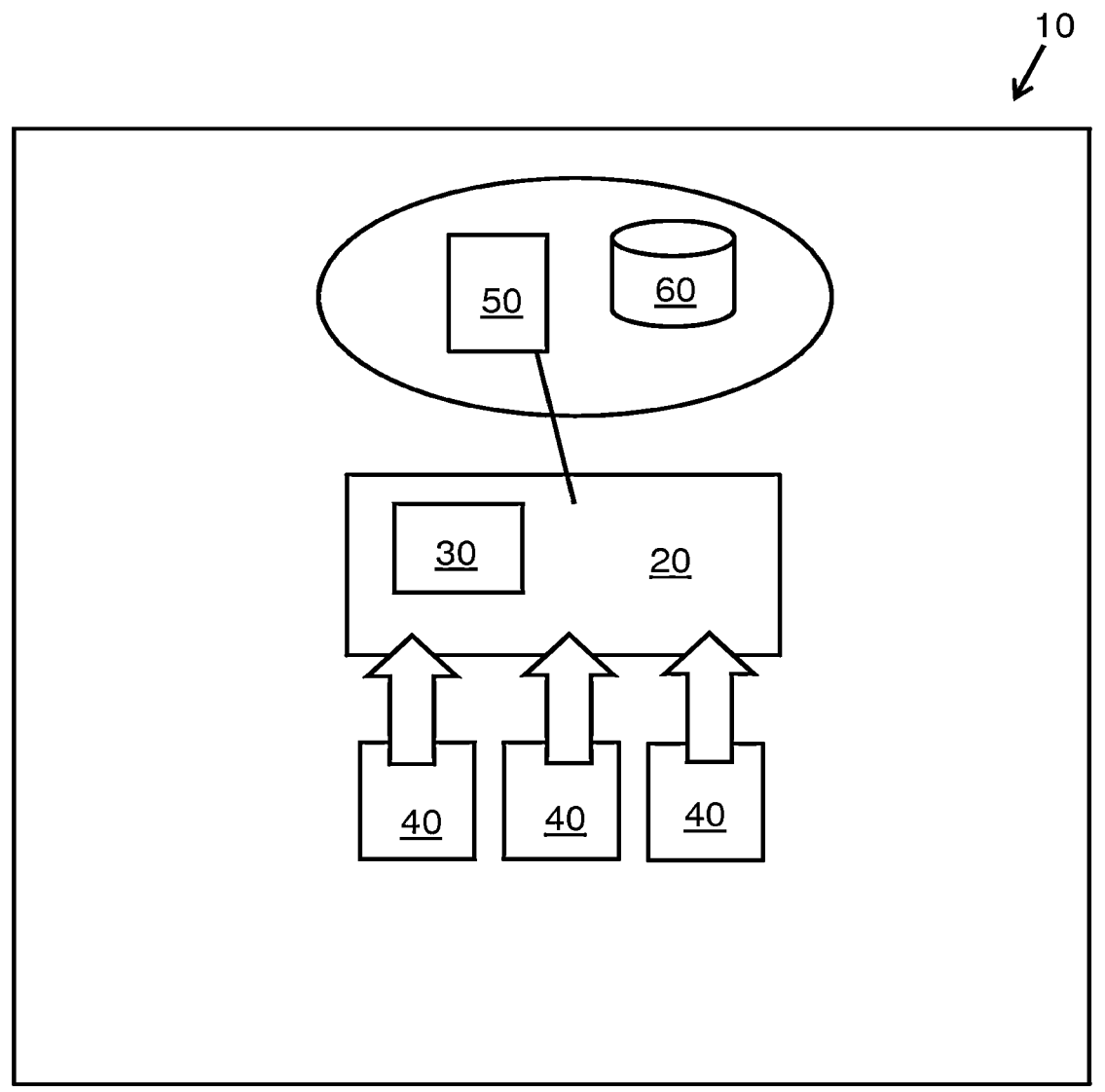
FIG. 1 is a schematic illustration of a data processing system pursuant to the present disclosure.

In the accompanying diagrams, an underlined number is employed to represent an item over which the underlined number is positioned or an item to which the underlined number is adjacent.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

A virtual file is a file (or directory) that is not actually present on a computer system's file system. Whereas a virtual file system may comprise an entire file system tree of virtual files, a virtual file may additionally appear to be located at a path within an existing real file system, even though the virtual file is not actually present on the real file system.

File systems, including virtual file systems, are required by POSIX-compliant Operating Systems to be mounted at a path, usually by privileged users. In contrast, a FUSE system in Linux® allows a non-privileged user to mount file systems, including virtual file systems, at a path with the assistance of the FUSE kernel model. However, this approach may not be accessible within tighter security privileges of a container-environment such as Docker®, without explicit relaxation of these restrictions. When one user mounts such a file system, its presence is also generally visible to all other users, which may not be desirable.

In some circumstances, it is useful to be able to make a virtual file system available that either (a) works without a system mount point, (b) works in-place within the existing mounted file systems, and/or (c) can work with restricted privileges such as found in restricted environments like Docker®.

An alternative approach to using mounted virtual file systems, is to use Dynamic Linking to intercept and modify accesses by an executable to the file system. Such a mechanism includes LD_PRELOAD in Linux-based systems and DLYD_INSERT_LIBRARIES for BSD-based systems including Mac OS. Here, upon loading the executable, resolving of symbols to dynamic libraries such as glibc.so used by most Linux executables to access file systems, can be intercepted by an alternate supplied library, providing matching symbol names. The alternate library can intercept calls by the executable to the matching symbols, so as to alter the functionality of those symbols, which in turn alters the overall behaviour of the executable. For example, an 'open64' symbol is assumed by an executable to allow opening of a file for subsequent accesses, and returns a file-handle. The alternate library can intercept calls to this symbol so as to provide alternate behaviour, such as opening a different file from the one initially specified. This interception mechanism for file-system accesses has the advantage of not requiring any special privileges, and enables virtual files to appear to reside within existing mounted file-systems. However, such an interception mechanism for file-system accesses has a number of shortcomings that has not made it practical for general use.

The shortcomings are:

1. Although file system accesses can readily be intercepted by hooking into operations such as open, read and write, memory-mapped files have their read/write operations handled by the operating system which directly reads/writes data to the file-system through the kernel, thus not allowing interception by the library.

2. Statically-compiled binaries, or binaries which do not use libraries such as glibc.so to access the file system, but instead directly invoke operating system calls, cannot be intercepted by this Dynamic Linking mechanism.

In overview, referring to FIG. 1, there is provided a data processing system 10 a data processing arrangement 20, wherein the data processing arrangement 20 includes computing hardware 30 for executing one or more software products 40, wherein execution of the one or more software products 40 configures the data processing arrangement to access data from a file system arrangement, characterized in that the data processing arrangement 10 is operable to load a dynamic linker 50 that is operable to include an intercept library 50 that intercepts file access operations of an executable software product wherein:

- (i) a virtual file that does not exist on the file system arrangement becomes accessible to the executable software product;
- (ii) the virtual file is a result of either (a) a just-in-time translation of one or more real files of the file system arrangement, wherein the just-in-time translation is made from one file format to another file format, or (b) conversion of the access operation to an equivalent cloud object-storage access operation(s) on a real object located on the cloud object-storage, or (c) a combination of the just-in-time translation of (a) with the object access conversion from (b).

Optionally, in the data processing system, at least one of:

- (iii) the virtual file is a different file format to the real file/object, wherein a compressed file format and the virtual file are mutually different file formats; and
- (iv) the file formats are genomic file formats.

Optionally, the compressed file format is a compressed genomic file format, and another file format is another genomic file format.

The bulk of genomic data is already compressed in standard formats as either BAM or FASTQ.gz files, utilising ZLIB/GZIP-based compression technology. As individual files can be many GBs (Gigabytes) and sometimes TBs (Terabytes) in size, organisations have the challenge of storing and transferring these files. Better compression would be advantageous in reducing the cost of storage and the time for data transfers. However, compressing to a new or updated file format necessarily breaks compatibility with the existing ecosystem of bioinformatics tools and pipelines that do not support this new file format. While it is possible to decompress back to the original file format (such as BAM or FASTQ.gz) and then feed these into the tools and pipelines, this needs to be specified explicitly as part of the pipeline, or time must be taken to first decompress the entire file before processing, even when only a small portion is actually used for the analysis. For this reason, it is desirable to be able to transparently convert from the new better-compressed file format, to the less-compressed, but widely compatible file format.

Another issue with processing genomic data is that pipelines are composed of executables that can read/write storage via POSIX file accesses, and are not built for reading or writing to cloud storage which usually operate via REST accesses. It would be advantageous if these tools/pipelines could access cloud storage as though they were regular files.

Optionally, in the data processing system, the dynamic linker includes the intercept library in a forceful manner.

Optionally, in the data processing system, the executable software product is operable to access genomic data via use of a ptrace call, wherein the ptrace call allows for manipulation of file descriptors, data memory and data registers. More optionally, in the data processing system, the ptrace call is operable to intercept forcibly calls made by the data processing system of a child process that is executable by intercepting file system calls via a kernel-provided executable tracing function wherein:

- (i) a virtual file that does not exist on the file system arrangement is made accessible to the data processing system;
- (ii) the virtual file is a just-in-time translation of one or more files on the file system arrangement from one file format to another file format;
- (iii) the real file is a compressed genomic file format and the virtual file is another genomic file format; and

- (iv)(*) in operation, a system call for opening the virtual file is intercepted, and firstly handled by ensuring that a virtual file system mount is available, and redirecting the system call to a file on the virtual file system instead.

Optionally, the data processing system is operable to intercept file system accesses of a child process so as to provide access to virtual files to the child process, wherein the data processing system is operable to:

- (i) intercept a library using a Dynamic Linking interception mechanism such as LD_PRELOAD;
- (ii) intercept calls in the library for creating a new child process (for example, by intercepting exec variants, such as execve, and fork/vfork in Linux);
- (iii) examine the executable of the new child process to determine whether or not it has dependencies on an appropriate intercept library (for example, by checking if it has a dynamic dependency on glibc.so), and wherein:

- (iv) if the child process has dependencies on the intercept library, then allowing the child process to be created, but ensuring that the Dynamic Library interception mechanism is enabled (for example, by ensuring that the LD_PRELOAD environment variable includes the requisite interception library), wherein the requisite intercept library intercepts file-system accesses so as to provide the virtual files; or
- (v) if the child executable does not have dependencies on the intercept library, then checking to see whether an alternate interception mechanism is available (i.e. whether the parent process has sufficient privileges to apply the alternate interception method), wherein if the alternate interception mechanism is available, then applying the alternate interception mechanism to the child process.

Optionally, if multiple such alternate interception mechanisms are available, then the data processing system is operable to choose one such available alternate interception mechanism.

Optionally, the alternate interception mechanism allows the child process to proceed, but sets up interception system calls of the child process (for example, by using the ptrace mechanism in Linux). More optionally, for performance, the interception of system calls are restricted to only those of interest (for example, by using seccomp filters on Linux). In this manner, all file-system operations can be intercepted such that any operations on virtual files are translated.

Optionally, the alternate interception mechanism is to utilise a Just-In-Time recompiler (such as Intel's PIN tool or HP-MIT's DynamoRIO) operating on the child process, wherein the Just-In-Time recompiler is configured to detect and intercept system calls by the child process. In this manner, system calls that access the file-system can be redirected to alternative code that provides the virtual files.

Optionally, the data processing system is operable to redirect any filename-based (or pathname-based) access to a virtual file, to an equivalent entry within a virtual file system mount point (such as, a FUSE mount to a temporary restricted access directory for Linux), wherein if no such mount point is currently present, a new mount is created Just-In-Time prior to the modified system call being invoked. In this scheme, the system call for operations such as 'open file' would return a valid file handle, wherein the read/write operations on that file handle would not need further system-call interception, thus improving performance, but would instead be intercepted via the mount-based Virtual File System method.

More optionally, in the data processing system, in (iv)(*), the virtual file system mount is implemented as a temporary directory, wherein, if the mount point is not already present, the data processing system is operable automatically to create the mount point with the virtual file system so that it is present.

Optionally, in the data processing system, the dynamic linker is operable to intercept the system calls of a child process executable by just-in-time recompiliation of sections of binary code just before binary code is run, wherein:

(i) the virtual file that does not exist on the file system arrangement is made accessible;

(ii) the virtual file is a just-in-time translation of one or more real files on the file system arrangement, wherein the just-in-time translation is made from one file format to another file format (iii) the real file is a compressed genomic file format and the virtual file is another genomic file format; and (iv) a system call for opening the virtual file is intercepted, and handled by firstly ensuring that a virtual file system mount is available, and then redirecting the system call to a file on the virtual file system instead.

More optionally, in data processing system, the virtual file system mount is implemented as a temporary directory, wherein there is automatically created a mount point with the virtual file system so that it is present.

Optionally, in the data processing system, the just-in-time translation of a transparent access of genomic data is operable to combine content from multiple genomics files and present it as one genomic file, for any one or combination of:

(i) wherein the merged content is quality score data;

(ii) wherein the merged content is read name information;

(iii) wherein the merged content is auxiliary tags of mapped genomic reads;

(iv) wherein the merged content consists of separate genomic regions;

(v) wherein the merged content consists of multiple genomic samples/specimens; and (vi) wherein the separate genomic files represent different regions, samples or other separable parts of a given genome.

Optionally, in the data processing system, the dynamic linker is forcibly loaded and employs in operation an intercept library that intercepts file access operations of an executable software product wherein:

(i) the creation of a new child process preserves an intercept library in an associated interception environment variable.

Optionally, in the data processing system, the dynamic linker is operable to employ an intercept library that intercepts file access operations of an executable software product wherein:

(i) the intercept library detects if a program is being submitted to a job submission system, and if so:

(ii) a temporary shell script is created that preserves an interception environment variable prior to calling an original program; and (iii) there is submitted the new temporary script to the job submission system, instead of the original program More optionally, in the data processing system, before implementing (iii), the data processing system is operable to:

(iv) detect if the original program is a script containing job-submission-system specific metadata, and if so copy this metadata information to a new temporary shell script.

Optionally, the data processing system is operable to provide transparent access of genomic data, such that accesses under a virtual path (for example, /pgs3/) are redirected to a cloud storage arrangement by translating operations to equivalent translated requests that are sent over the Internet to a cloud storage arrangement provider.

There are also compound concerns, where accessing genomic data on cloud storage presents challenges not just in the ability for tools and pipelines to directly stream access from cloud storage, but also suffers considerable delays and costs due to the bulkiness of the genomic data.

It would be advantageous if the objects in cloud storage utilised better-compressed file formats, and are Just-In-Time translated to the standard file format. In such a scheme, the file-system accesses to the standard file format are converted into equivalent cloud accesses to the better-compressed file format. Due to the better compression, less data would then be needed to be transferred from the cloud object storage, thus accelerating the access, at the cost of a computational overhead for translating the better-compressed data to the form of the standard file format.

More optionally, in the data processing system:

(i) a corresponding virtual file that does not exist on the cloud storage arrangement is accessible to the data processing system;

(ii) the virtual file is a just-in-time translation of one or more corresponding real objects on the cloud storage arrangement from one file format to another file format;

(iii) the real object is a compressed genomic file format and the virtual file is another genomic file format.

Optionally, the data processing system is operable to provide transparent access of genomic data, such that dynamic linker is operable to provide the intercept library for memory-mapped file access operations of an executable to a virtual file by:

(i) registering a page fault interrupt handler;

(ii) creating a virtual region of size as requested by a memory-mapped file mapping operation, but protected to prevent reads and writes;

(iii) on read access of one or more given protected pages, replacing the one or more pages with corresponding translated content from the real file, and allowing the one or more given protected pages to be accessible for reads and/or writes; and (iv) maintaining a list of the one or more pages of translated content, and upon hitting a memory consumption limit free up memory taken by translated content, choosing one or more pages of the translated content, freeing memory of the one or more pages and protecting these page regions again to prevent further reads and writes; and (v) wherein a choice of which page to free is made by employing a LRU (least recently used), LFU (least frequently used) or other replacement heuristic.

Optionally, the data processing system is operable to provide transparent access of genomic data such that it intercepts the dynamic linker and is operable to provide the intercept library to enable memory-mapped file access operations of an executable to a virtual file, wherein:

(i) a system call for memory-mapping the virtual file is intercepted, and handled firstly by ensuring that a virtual file system mount is available (perhaps in a temporary directory, here 'ensure' means that if the mount point is not already present, to automatically create said mount point with virtual file system so that it is present), and then redirecting the memory-mapping operation to a file on the virtual file system instead.

According to another aspect, there is provided a method of using a data processing system 10 including a data processing arrangement 20, wherein the data processing arrangement 20 includes computing hardware 30 for executing one or more software products 40, wherein execution of the one or more software products 40 configures the data processing arrangement 20 to access data from a file system arrangement, characterized in that the method includes operating the data processing arrangement to load a dynamic linker that is operable to include an intercept library that intercepts file access operations of an executable software product wherein:

(i) a virtual file that does not exist on the file system arrangement becomes accessible to the executable software product;

(ii) the virtual file is a result of either (a) a just-in-time translation of one or more real files of the file system arrangement, wherein the just-in-time translation is made from one file format to another file format, or (b) conversion of the access operation to an equivalent cloud object-storage access operation(s) on a real object located on the cloud object-storage, or (c) a combination of the just-in-time translation of (a) with the object access conversion from (b).

Optionally, in the method, at least one of:

(iii) the virtual file is a different file format to the real file/object, wherein a compressed file format and the virtual file are mutually different file formats; and (iv) the file formats are genomic file formats.

Optionally, both (iii) and (iv) apply in a given method of the present disclosure.

Optionally, the compressed file format is a compressed genomic file format, and another file format is another genomic file format.

Referring to FIG. 2, there is shown a slow chart of steps of a method that is implemented using the data processing system 10 of FIG. 1.

The method includes a first step 200 of providing a data processing system including a data processing arrangement, wherein the data processing arrangement includes computing hardware for executing one or more software products, wherein execution of the one or more software products configures the data processing arrangement to access data from a file system arrangement.

The method further includes a second step 210 of operating the data processing arrangement 10 to load a dynamic linker that includes an intercept library that intercepts file access operations of an executable software product wherein:

(i) a virtual file that does not exist on the file system arrangement becomes accessible to the executable software product;

(ii) the virtual file is a result of either (a) a just-in-time translation of one or more real files of the file system arrangement, wherein the just-in-time translation is made from one file format to another file format, or (b) conversion of the access operation to an equivalent cloud object-storage access operation(s) on a real object located on the cloud object-storage, or (c) a combination of the just-in-time translation of (a) with the object access conversion from (b).

Optionally, in the method of FIG. 2, at least one of:

(iii) the virtual file is a different file format to the real file/object, wherein a compressed file format and the virtual file are mutually different file formats; and (iv) the file formats are genomic file formats.

Optionally, both (iii) and (iv) pertain to the method of FIG. 2.

According to another aspect there is provided a computer program product comprising a non-transitory computer-readable storage medium having computer-readable instructions stored thereon, the computer-readable instructions being executable by a computerized device comprising processing hardware to execute the aforementioned method.

Modifications to embodiments of the present disclosure described in the foregoing are possible without departing from the scope of the present disclosure as defined by the accompanying claims. Expressions such as "including", "comprising", "incorporating", "consisting of", "have", "is" used to describe and claim the present invention are intended to be construed in a non-exclusive manner, namely allowing for items, components or elements not explicitly described also to be present. Reference to the singular is also to be construed to relate to the plural. Numerals included within parentheses in the accompanying claims are intended to assist understanding of the claims and should not be construed in any way to limit subject matter claimed by these claims.

The phrases "in an embodiment", "according to an embodiment" and the like generally mean the particular feature, structure, or characteristic following the phrase is included in at least one embodiment of the present disclosure, and may be included in more than one embodiment of the present disclosure. Importantly, such phrases do not necessarily refer to the same embodiment.

APPENDIX (INVENTOR'S NOTES)

A Transparent Access Layer

From Wikipedia entry on Dynamic Linker:

"The dynamic linker can be influenced into modifying its behaviour during either the program's execution or the program's linking, and the examples of this can be seen in the run-time linker manual pages for various Unix-like systems. A typical modification of this behaviour is the use of:

LD_LIBRARY_PATH and LD_PRELOAD environment variables, which adjust the runtime linking process by searching for shared libraries at alternate locations and by forcibly loading and linking libraries that would otherwise not be, respectively. An example is Zlibc®, also known as "uncompress.so", which facilitates transparent decompression when used through the LD_PRELOAD hack; as a result, it is possible to read pre-compressed (gzipped) file data on BSD and Linux® systems as if the files were not compressed, essentially allowing a user to add transparent compression to the underlying filesystem, although with some caveats. The mechanism is flexible, allowing trivial adaptation of the same code to perform additional or alternate processing of data during the file read, prior to the provision of said data to the user process that has requested it."

Transparent Access of Genomic Data (Main Method)

Method:

Forcibly loading, via a Dynamic Linker, an intercept library that intercepts the file access operations of an executable such that:

(i) a virtual file that does not exist on the file-system is accessible;

(ii) wherein the virtual file is a just-in-time translation of a real file(s) on the file-system from one file format to another file format; and

(iii) wherein the real file is a compressed genomic file format and the virtual file is another genomic file format.

Alternate Method 1 of Transparent Access of Genomic Data:
Using system-call interception, such as via ptrace.
From Wikipedia entry on ptrace:

"ptrace is used by debuggers (such as qdb and dbx), by tracing tools like strace and ltrace, and by code coverage tools. ptrace is also used by specialised programs to patch running programs, to avoid unfixed bugs or to overcome security features. It can further be used as a sandbox and as a runtime environment simulator (like emulating root access for non-root software).

By attaching to another process using the ptrace call, a tool has extensive control over the operation of its target. This includes manipulation of its file descriptors, memory, and registers. It can single-step through the target's code, can observe and intercept system calls and their results, and can manipulate the target's signal handlers and both receive and send signals on its behalf. The ability to write into the target's memory allows not only its data store to be changed, but also the application's own code segment, allowing the controller to install breakpoints and patch the running code of the target."

Prior art on this type of access method but that does not do translation or virtual file systems:

http://www.alfonsobeato.net/c/modifying-system-call-arguments-with-ptrace/ http://www.alfonsobeato.net/c/filter-and-modify-system-calls-with-seccomp-and-ptrace/

Method:

Forcibly intercepting the system calls of a (child process) executable by intercepting file system calls via kernel-provided executable tracing function such that:

(i) a virtual file that does not exist on the file-system is accessible;

(ii) wherein the virtual file is a just-in-time translation of a real file(s) on the file-system from one file format to another file format;

(iii) wherein the real file is a compressed genomic file format and the virtual file is another genomic file format; and (iv) wherein a system call for opening said virtual file is intercepted, and handled by first ensuring that a virtual file system mount is available (perhaps in a temporary directory, here 'ensure' means that if the mount point is not already present, to automatically create said mount point with virtual file system so that it is present), and redirecting the system call to a file on said virtual file system instead.

Alternate Method 2 of Transparent Access of Genomic Data:
This is based on instrumentation such as by Intel's PIN.
From Wikipedia entry on PIN:

"Pin performs instrumentation by taking control of the program just after it loads into the memory. Then just-in-time recompiles (JIT) small sections of the binary code using pin just before it is run. New instructions to perform analysis are added to the recompiled code. These new instructions come from the Pintool. A large array of optimization techniques are used to obtain the lowest possible running time and memory use overhead. As of June 2010, Pin's average base overhead is 30 percent (without running a pintool)."

Method:

Forcibly intercepting the system calls of a (child process) executable by just-in-time recompiliation of sections of the binary code just before it is run, such that:

(i) a virtual file that does not exist on the file-system is accessible;

(ii) wherein the virtual file is a just-in-time translation of a real file(s) on the file-system from one file format to another file format;

(iii) wherein the real file is a compressed genomic file format and the virtual file is another genomic file format; and (iv) wherein a system call for opening said virtual file is intercepted, and handled by first ensuring that a virtual file system mount is available (perhaps in a temporary directory, here 'ensure' means that if the mount point is not already present, to automatically create said mount point with virtual file system so that it is present), and redirecting the system call to a file on said virtual file system instead.

Note that like the main method for interception, the Alternate methods can also work by intercepting actual file read (write) and seek operations to the virtual file rather than just the file open operation. However (iv) also allows a more efficient interception method so that the file-open operation is redirected to a path on a mounted virtual file system (e.g. FUSE under Linux), and so that the actual file read and seek operations are intercepted at the mounted virtual file system layer, instead of via intercepting the corresponding system calls.

Decision Between the Two Methods of Accessing Genomic Data:

Method:

Wherein the executable being intercepted is examined to see if it has a dynamic library dependency on an interceptable library (such as glibc) and if not, then an alternate access method is used instead of the main method. The alternate method can itself be chosen based on whether the Alternate method 1 is available for use on the executable (i.e. if there are sufficient user security privileges) and if not using the Alternate method 2 instead.

Transparent Access of Tiered/Separated Genomic Data
Method:

Wherein the just in time translation of the transparent access of genomic data (and alternates) can combine content from multiple genomics files and present it as one genomic file, for any one or combination of:

(i) Wherein the merged content is quality score data;

(ii) Wherein the merged content is read name information;

(iii) Wherein the merged content is auxiliary tags of mapped genomic reads;

(iv) Wherein the merged content consists of separate genomic regions; and (v) Wherein the merged content consists of multiple genomic samples/specimens;

Wherein the just in time translation of the transparent access of genomic data (and alternates) can take one genomic file and present it as multiple genomic files:

(i) wherein the separate genomic files represent different regions, samples or other separable parts of the genome.

Protect Interception Ability with Child Processes

In Linux, the LD_PRELOAD environment variable can be configured to load an interception library, however this means that if the environment variable is modified by a process or if a child process is invoked without it, then the interception capability is lost. Similar environment variables exist in MacOS and BSD-based operating systems. We will call these interception environment variables.

Method:

Forcibly loading, via a Dynamic Linker, an intercept library that intercepts the file access operations of an executable such that:

(i) the creation of a new (child) process preserves the intercept library in the interception environment variable.

Protect Interception Ability with Job Submission Systems

Job submission systems (such as for HPC systems) may not preserve interception environment variables for a job submission due to it being considered a security risk.

Method:

Forcibly loading, via a Dynamic Linker, an intercept library that intercepts the file access operations of an executable such that:

(i) it detects if a program is being submitted to a job submission system, and if so;

(ii) a temporary shell script is created that preserves the interception environment variable prior to calling the original program;

(iii) optionally detecting if the program is a script containing job-submission-system specific metadata, and if so copying this metadata information to the new temporary shell script; and (iv) submitting the new temporary script to the job submission system, instead of the original program.

Extensions for Cloud Storage

That enables access to/from cloud (e.g. AWS S3) storage as virtual files. Unlike prior art, this is via the above interception methods and with a virtual file with different file format to the underlying object file format.

Method:

As per the transparent access of genomic data (and alternatives) such that accesses under a virtual path (e.g. /pgs3/) are redirected to cloud storage by translating operations to equivalent translated requests that are sent over the internet to the cloud storage provider and such that:

(i) a corresponding virtual file that does not exist on the cloud storage is accessible;

(ii) wherein the virtual file is a just-in-time translation of a corresponding real object(s) on the cloud storage from one file format to another file format; and (iii) wherein the real object is a compressed genomic file format and the virtual file is another genomic file format.

For example, accesses to/pgs3/mybucket/myfile.bam are redirected to an object that exists at cloud object location s3://mybucket/myfile.cram (with a different file format), and where a corresponding object at s3://nnybucket/myfile.bam does not exist.

Handling Memory Mapped Files

Unfortunately accesses to memory-mapped files are harder to handle in the case of forcibly loading, via a Dynamic Linker, an intercept library that intercepts the file access operations of an executable. This is because such file accesses are meant to occur by merely accessing a memory location within the region of a memory-mapped file, rather than as a call to an interceptable library function.

Method:

As per the Transparent access of genomic data (and alternates) such that it intercepts the memory-mapped file access operations of an executable to a virtual file by:

(i) Registering a page fault interrupt handler;

(ii) Creating a virtual region of size as requested by memory-mapped file mapping operation, but protected to prevent reads and writes;

(iii) On read access of a said protected page, replacing the page (and optionally surrounding pages, or optionally prefetching subsequent pages) with corresponding translated content from the real file, and allowing said page(s) to be accessible for reads (and/or writes);

(iv) Maintaining a list of said pages of translated content, and upon hitting a memory consumption limit free up memory taken by translated content, choosing a page (or pages) of said translated content, freeing memory of said page(s) and protecting these page regions again to prevent further reads and writes; and (v) wherein the choice of which page to free is by a LRU (least recently used), LFU (least frequently used) or other replacement heuristic.

Alternate Method for Handling Memory Mapped Files

As per the Transparent access of genomic data (and alternates) such that it intercepts the memory-mapped file access operations of an executable to a virtual file:

(i) wherein a system call for memory-mapping said virtual file is intercepted, and handled by first ensuring that a virtual file system mount is available (perhaps in a temporary directory, here 'ensure' means that if the mount point is not already present, to automatically create said mount point with virtual file system so that it is present), and redirecting the memory-mapping operation to a file on said virtual file system instead.

I claim:

1. A data processing system, comprising:

a data processing arrangement comprising computing hardware, the data processing arrangement configured to access data from a file system arrangement, wherein the data processing arrangement uses a dynamic linker that uses an intercept library to intercept file access operations of an executable software product, wherein the intercept library employs multiple interception mechanisms, including a first interception mechanism to intercept dynamic binaries and a second interception mechanism different from the first interception mechanism, wherein the intercept library is arranged to implement the second interception mechanism by using at least one of: a combination of PTRACE and FUSE, a combination of PTRACE and SECCOMP filtering, or Dynamic Binary Instrumentation, and wherein the intercept library employs the first interception mechanism to intercept a launch by a parent process of a new child process associated with an executable binary; and a computer-readable storage medium storing computer-readable instructions that, when executed by the computing hardware, cause the data processing arrangement to perform:

(a) intercepting, using the intercept library, the launch of the new child process by the parent process;

(b) determining whether the executable binary has a dependence on an operating system library; and (c) responsive to a determination in step (b) that the executable binary has no dependence on the operating system library, using the second interception mechanism to intercept file system calls made by the new child process for accessing a virtual file that does not exist on the file system arrangement.

2. The data processing system of claim 1, wherein the intercept library, when in operation, intercepts static or dynamic child binary processes, or both, to provide a virtual file system for object storage.

3. The data processing system of claim 1, wherein the intercept library is arranged to implement the first interception mechanism by using LD_PRELOAD.

4. The data processing system of claim 1, wherein the second interception mechanism is chosen based on security or capability privileges available to the parent process.

5. The data processing system of claim 1, wherein the virtual file is a result of conversion of the accessing by the new child process to one or more equivalent object-storage access operations on a real object located on object-storage.

6. The data processing system of claim 1, wherein the second interception mechanism is operable to intercept calls made by the new child process by intercepting file system calls via a kernel-provided executable tracing function, wherein the virtual file that does not exist on the file system arrangement is made accessible to the data processing system via another virtual file system in a separate path, and in operation, a system call for opening the virtual file is intercepted, and is firstly handled by ensuring that a virtual file system mount is available, and redirecting the system call to a file said another virtual file system instead.

7. The data processing system of claim 6, wherein the virtual file system mount is implemented as a temporary directory, wherein there is automatically created a mount point with the virtual file system so that the mount point is present.

8. The data processing system of claim 1, wherein the dynamic linker employs, when in operation, the intercept library that intercepts file access operations of the executable software product, wherein creation of the new child process preserves the intercept library in an associated interception environment variable.

9. The data processing system of claim 1, wherein accesses, by the data processing system, under a virtual path are redirected, by the data processing system, to a cloud storage arrangement by translating operations to equivalent translated requests that are sent over the Internet to the cloud storage arrangement.

10. The data processing system of claim 1, wherein the data processing system is operable to provide transparent access of data, such that the data processing system uses the intercept library to enable memory-mapped file access operations of an executable to a virtual file, wherein a system call for memory-mapping the virtual file is intercepted, and handled by first ensuring that another virtual file system at a separate mount is available, and redirecting the memory-mapping operation to a file on said another virtual file system instead.

11. A method for operating a data processing system including a data processing arrangement comprising computing hardware, wherein the data processing arrangement, when in operation, is configured to access data from a file system arrangement at least in part by using a dynamic linker that uses an intercept library to intercept file access operations of an executable software product, wherein the intercept library is configured to employ multiple interception mechanisms, including a first interception mechanism to intercept dynamic binaries and a second interception mechanism different from the first interception mechanism, wherein the intercept library is arranged to implement the second interception mechanism by using at least one of: a combination of PTRACE and FUSE, a combination of PTRACE and SECCOMP filtering, or Dynamic Binary Instrumentation, wherein the intercept library employs the first interception mechanism to intercept a launch by a parent process of a new child process associated with an executable binary, the method comprising:

(a) intercepting, using an intercept library, the launch of the new child process by the parent process;

(b) determining whether the executable binary has a dependence on an operating system library; and (c) responsive to a determination in step (b) that the executable binary has no dependence on the operating system library, using the second interception mechanism to intercept file system calls made by the new child process for accessing a virtual file that does not exist on the file system arrangement.

12. The method of claim 11, wherein the intercept library, when in operation, intercepts static or dynamic child binary processes, or both, to provide a virtual file system for object storage, wherein the object storage is accessible by a cloud storage application programming interface (API).

13. The method of claim 11, wherein the intercept library is arranged to implement the first interception mechanism by using LD_PRELOAD.

14. The method of claim 11, wherein the second interception mechanism is chosen based on security or capability privileges available to the parent process.

15. The method of claim 11, wherein the virtual file is a result of conversion of the accessing by the new child process to one or more equivalent object-storage access operations on a real object located on object-storage.

16. At least one non-transitory computer-readable storage medium storing computer-readable instructions that, when executed by a computerized device, cause the computerized device to perform a method for operating a data processing system including a data processing arrangement which, when in operation, is configured to access data from a file system arrangement at least in part by using a dynamic linker that uses an intercept library to intercept file access operations of an executable software product, wherein the intercept library is configured to employ multiple interception mechanisms, including a first interception mechanism to intercept dynamic binaries and a second interception mechanism different from the first interception mechanism, wherein the intercept library is arranged to implement the second interception mechanism by using at least one of: a combination of PTRACE and FUSE, a combination of PTRACE and SECCOMP filtering, or Dynamic Binary Instrumentation, wherein the intercept library employs the first interception mechanism to intercept a launch by a parent process of a new child process associated with an executable binary, the method comprising:

(a) intercepting, using an intercept library, the launch of the new child process by the parent process;

(b) determining whether the executable binary has a dependence on an operating system library; and (c) responsive to a determination in step (b) that the executable binary has no dependence on the operating system library, using the second interception mechanism to intercept file system calls made by the new child process for accessing a virtual file that does not exist on the file system arrangement.

17. The at least one non-transitory computer-readable storage medium of claim 16, wherein the intercept library is arranged to implement the first interception mechanism by using LD_PRELOAD.

18. The at least one non-transitory computer-readable storage medium of claim 16, wherein the virtual file is a result of conversion of the accessing by the new child process to one or more equivalent object-storage access operations on a real object located on object-storage.

* * * * *